US 6,685,680 B2

(12) United States Patent
Utterberg et al.

(10) Patent No.: US 6,685,680 B2
(45) Date of Patent: *Feb. 3, 2004

(54) TAPERED INTRAVENOUS CANNULA

(75) Inventors: David S. Utterberg, Seattle, WA (US); William J. Schnell, Libertyville, IL (US)

(73) Assignee: DSU Medical Corporation, Las Vegas, NV (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/906,539

(22) Filed: Jul. 16, 2001

(65) Prior Publication Data

US 2002/0032416 A1 Mar. 14, 2002

Related U.S. Application Data

(62) Division of application No. 09/295,024, filed on Apr. 20, 1999.

(51) Int. Cl.[7] ................................................. A61M 5/00
(52) U.S. Cl. ..................................................... 604/264
(58) Field of Search ........................... 604/93.01, 506, 604/502, 264, 265, 236, 239, 272–274, 526, 164.03, 900

(56) References Cited

U.S. PATENT DOCUMENTS

| 3,598,126 A | * | 8/1971 | Hoeltzenbein .............. 604/526 |
| 4,181,132 A | | 1/1980 | Parks |
| 4,874,373 A | * | 10/1989 | Luther et al. .......... 604/164.03 |
| 4,955,861 A | | 9/1990 | Enegren et al. |
| 5,562,617 A | | 10/1996 | Finch, Jr. et al. |
| 5,658,260 A | | 8/1997 | Desecki et al. |
| 5,931,829 A | * | 8/1999 | Burbank et al. ............. 604/264 |
| 6,007,516 A | | 12/1999 | Burbank et al. |
| 6,120,492 A | | 9/2000 | Finch et al. |
| 6,245,052 B1 | * | 6/2001 | Orth et al. .................. 604/506 |

FOREIGN PATENT DOCUMENTS

| WO | WO 97/47338 | 12/1997 |
| WO | WO 98/31416 | 7/1998 |
| WO | WO 99/03527 | 1/1999 |

* cited by examiner

Primary Examiner—Manuel Mendez
Assistant Examiner—Mark K. Han
(74) Attorney, Agent, or Firm—Seyfarth Shaw LLP

(57) ABSTRACT

A cannula and method for providing an external connection with an implanted artificial port for communicating with a body lumen of a patient. The artificial port has an entrance conduit with an inwardly tapering section. The tapered cannula is sized and proportioned to substantially match and seal with the inwardly tapering section of the entrance conduit. Thus the cannula can form a readily removable seal with the inwardly tapering section. A typical angle of taper is one to three degrees.

18 Claims, 4 Drawing Sheets

TAPERED INTRAVENOUS CANNULA

This is a divisional application of Ser. No. 09/295,024, filed Apr. 20, 1999

BACKGROUND OF THE INVENTION

This invention relates to an improved cannula for communication with the vascular system in order to gain access to a supply of blood for extracorporeal blood processing, for example hemodialysis, hemoperfusion, or any other desired form of extracorporeal blood treatment.

In the early days of dialysis therapy, extracorporeal blood flows were moderate, at about 200 ml/min. with the result that a dialysis treatment took six hours or more. These treatments, while long, were often uneventful, not least because the extracorporeal pressures were moderate with the low flow rates, typically between −120 mm./Hg (arterial) and +120 mm./Hg (venous). Modern therapy has increased the flow rates to as much as 500 ml./min. or more, with corresponding increases in treatment efficiency. However, the operating pressures have also increased, even to as much as −400 mm./Hg (arterial) and as much +600 mm./Hg (post pump). At these pressures, undesirable events can take place more readily, for example, hemolysis, foaming or clotting of the blood, air emboli, and other alarm conditions, which may be frequent and sometimes severe.

While the operating pressures could be reduced by increasing the inner diameter of the patient access cannulae, which are typically the narrowest portion of the extracorporeal blood circuit, an increase in the size of the needles, which could significantly reduce pressures, is strongly objected to by the patients. A large needle results in a larger incision. Patients have historically shown reluctance to be penetrated in a fresh site by a needle with a cutting point larger than 15 G (gauge).

By this invention, a vascular cannula is provided, which is capable of passing high blood flow rates at reduced pressures without significant enlargement of the distal end portion of the cannula that penetrates the patient's skin and vascular system. The cannula of this invention is particularly desirable for use in conjunction with implanted artificial access ports for the vascular system. For example, as shown in Finch et al. U.S. Pat. No. 5,562,617, Enegren et al. U.S. Pat. No. 4,955,861, or International Publication WO97/47338.

DESCRIPTION OF THE INVENTION

By this invention, a cannula is provided for communication typically with the vascular system of the patient. The cannula has a proximal end connected with a blood flow tube, the cannula having an inward taper between the proximal end and a distal end, whereby the distal end is of less diameter than the proximal end. The distal end is pointed, beveled or not beveled, but is blunt enough to be effectively incapable of cutting through intact, human skin (for example at forces of less than 100 gm.) being preferably advanced through the skin to an implanted vascular access port by means of a preformed track through the tissue that does not require a sharp forward cutting edge on the cannula, or an accompanying trocar, in a manner similar to that disclosed in Vasca Inc. International Publication No. WO99/03527.

Preferably, the cannula is rigid, being made of a surgical steel, copolymer plastic, or the like, in which the inward taper extends substantially the entire cannula length.

Thus, substantial portions of the cannula have an enlarged inner diameter over that which penetrates the patient, which can have the effect of greatly reducing flow resistance through the system (since pressure resistance has a fourth power, inverse relationship to the inner diameter of a flow passageway).

The subsequent discussion of gauges and tapers is relevant for hemodialysis wherein flows are relatively high, (for example from 180 ml/min to 60 ml/min and more. This invention is also valuable for other low-flow applications such as chemotherapy (for example, from 20 ml/min to 0.5 ml/min or less). In such latter case a properly sized tapered cannula may preferably be from 25 G to 21 G, or anything in between, at its distal end. Other uses of implanted, artificial ports and tapered, blunt access cannulas may be for diabetes therapy, urinary ports, and the like, with different flow rates and cannula sizes contemplated, for example 15 G to 19 G at the distal end.

The taper may preferably define an angle of 1–3 or 4 degrees (per side) to the cannula longitudinal axis. Also preferably, the distal cannula end may be of 11–13 gauge and the proximal cannula end may be 14–15 gauge. The "gauge" measure is the well-known, commonly used system of the industry.

If desired, the cannula may have a single lumen, although multiple lumen cannulas may be used as well, and the lumen may receive a removable trocar. The trocar may have a blunt forward end, also effectively incapable of cutting through living tissue, to pass with the cannula along a preformed tissue track through the skin to an implanted vascular access port. Alternatively, the trocar may be straight or tapered, and may have a sharp end to assist the blunt-end cannula in advancing through tissue into communication with the vascular system of a patient.

As a further preferable advantage of a blunt non-beveled tapered cannula, the blunt cannulas can be made in mass production, but it has been technically and economically impractical to grind sharp or dull, beveled ends on tapered cannulas with conventional manufacturing equipment. Cannulas are typically ground in batches of two hundred or more while set in a jig. This is not practical in the conventional equipment with tapered cannulas. Accordingly, the use in accordance with this invention of a blunt, non-beveled, tapered cannula makes possible the large scale, commercial manufacture thereof with conventional manufacturing equipment, while achieving the advantages of reduced flow pressures at higher flow rates, which can be obtained by the use of tapered vascular cannulas.

Also, by this invention, external fluid connection with an implanted artificial port communicating with a body lumen of a patient may be achieved. The artificial port used in this invention may have an entrance conduit which comprises an inwardly tapering section of 1 degree to 4 degrees on each or all sides, most preferably about 1.4–2.6 degrees and more specifically about 1.6 to 1.7 degrees, from its longitudinal axis.

The method of this application comprises passing a tapered cannula through tissue of the patient into the entrance conduit. The tapered cannula may have a proximal end connected with a fluid flow tube, and preferably has a blunt distal end. The cannula may also have an inward taper of 1 to 4 degrees, on each or all sides, from its longitudinal axis between the proximal and distal ends. The inward taper is particularly sized and proportioned to substantially match (that is, be the same angle) and seal with the inwardly tapering section of the entrance conduit. Thus, the cannula can form a readily removable seal with the inwardly tapering section of the entrance conduit, in a manner similar to a well-known luer connector. However, it is believed that an implanted access port to a body lumen has never been used with a tapered cannula to form a luer connection.

Preferably, the tapered cannula has its inward taper over the majority of its length.

In a prior system of Vasca Inc. for connection between implanted ports and tubular sets ending in a cannula, the cannula is initially cylindrical, but makes a seal with an inwardly tapering section of an entrance conduit of an implanted artificial port. Substantial pressure is applied, causing actual deformation of the cannula, on the order of ten pounds applied between the cannula and the tapering section implanted in the patient, to form a seal by cannula deformation.

By this present method, the pressure imposed on the patient to make the connection is on the order of 40 percent or less of such heavy pressures, because by this invention there is no need for deformation of the tapered cannula or the inwardly tapering section to make an effective seal. Furthermore, this makes possible the disconnection and reconnection of the same cannula with the inwardly tapering section of the entrance conduit, since a good seal can be achieved without deformation, and which can be readily broken and then reestablished again if desired.

In order to reduce the torque and other pressures that are needed to break the tapered connection between the cannula of this invention and the inwardly tapering section of the entrance conduit, the inward taper of the tapered cannula may essentially match but be slightly less (on the order of 0.1 degree) than the degree of taper of the inwardly tapering section of the entrance conduit. In this circumstance, a reliable seal can be achieved that is more easily disconnected by twisting and removing of the cannula, when compared with the situation where the tapered cannula and the inwardly tapering section have exactly the same angle of taper. One can reduce this bonding strength of the tapered seal by increasing the difference between the inward taper of the tapered cannula from the degree of taper of the inwardly tapering section. One can also strengthen this bond by reducing the difference between the two tapered angles.

Because of the taper of the tapered cannula over preferably substantially its entire length, the beneficial results previously described of reduced flow resistance can be achieved. Particularly, the tapered cannula may preferably have a distal end of 11–13 G (gauge) and a proximal end of 14–15 G, as measured by the conventional gauge measurement system used in the industry.

The tapered cannula is preferably made of a medically acceptable, rigid material, for example, stainless steel or copolymer plastic.

DESCRIPTION OF SPECIFIC EMBODIMENTS

Figure 1A:
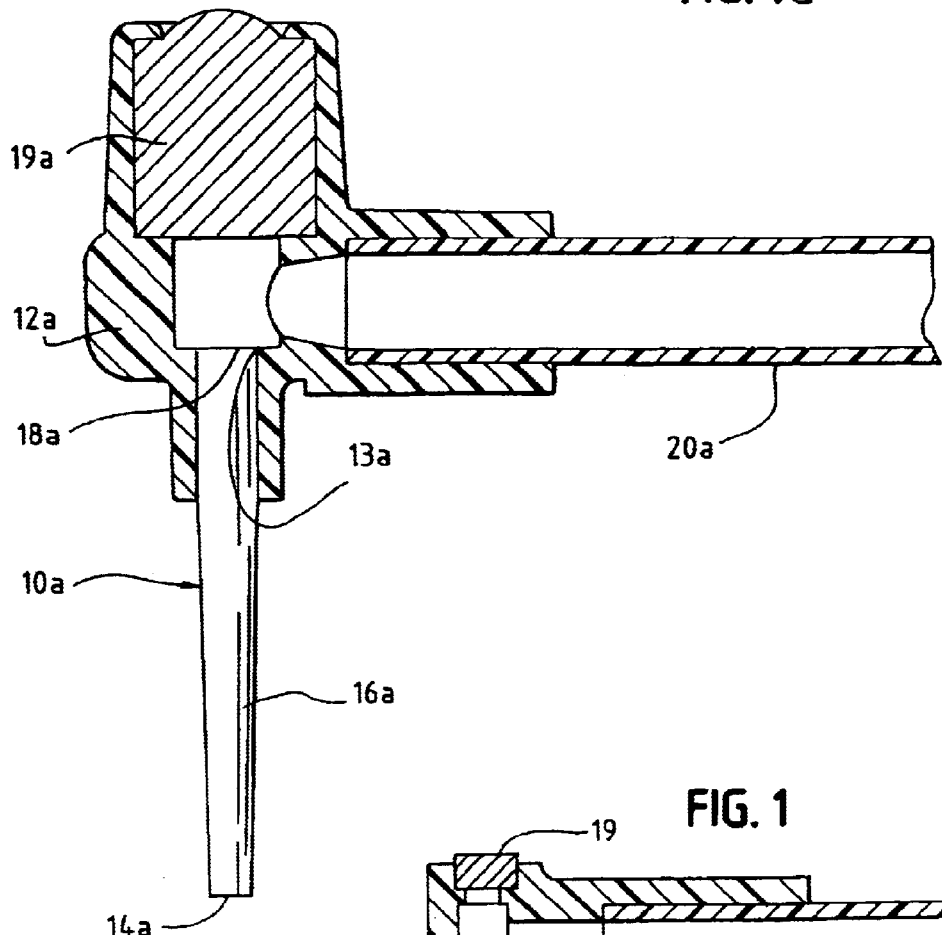
FIG. 1a is an elevational view of a modified cannula that is otherwise similar to FIG. 1.
Figure 1:
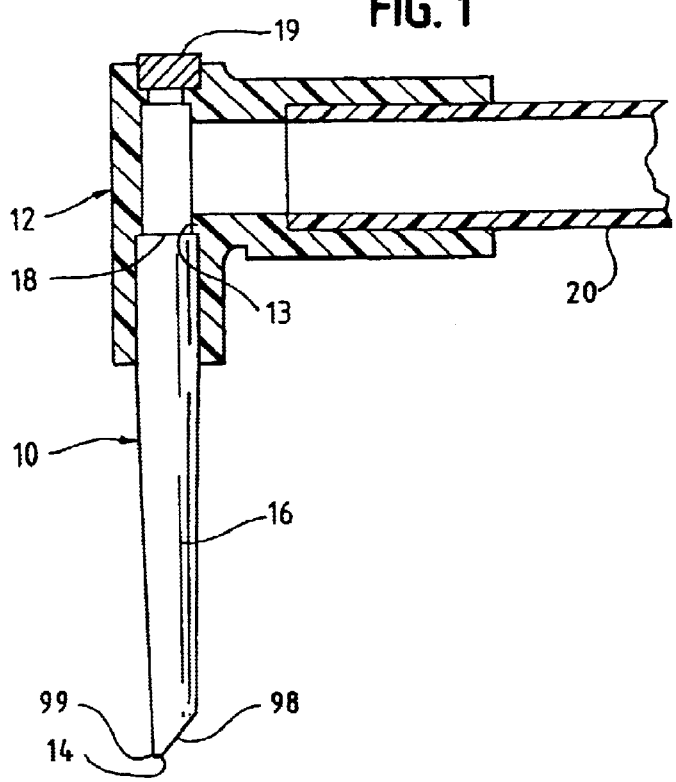
FIG. 1 is an elevational view of a cannula for communication with the vascular system of a patient, the cannula having a proximal end which is connected to a blood flow tube.

Referring to FIG. 1, a cannula 10 is provided, typically for communication with the vascular system of a patient for high flow hemodialysis, or the like. The cannula 10 comprises a tapered stainless steel tube in this specific embodiment, having a larger proximal end 13 that terminates in a hub 12 and has an inner diameter of 2.85 mm in this specific embodiment. Cannula 10 also has a distal end 14 which has an inner diameter of 1.85 mm, with the bore 16 of cannula 10 tapering in substantially uniform manner along its length from proximal end 12 to distal end 14. However, if desired, a cylindrical segment 18 of the cannula may be provided adjacent to the proximal cannula end 12.

The outer diameter of cannula 10 at distal end 14 may be about 2.1 mm. The wall thickness of cannula 10 adjacent to distal end 14 and typically along the remainder of the length of the cannula can be about 0.12 mm.

Distal end 14 carries a bevel 98, or a multi-bevel or compound bevel and ends in a point 99 that is dulled or blunt to provide dilation of a preformed track through the skin.

Steel cannula 10 is mounted in a hub 12, which may be made of molded plastic, and which also carries an injection site 19 and flexible tube 20, extending in this embodiment in a direction perpendicular to the longitudinal axis of cannula 10. Alternatively, hub 12 may carry a flexible tube which is coaxial with cannula 10, or extending at any desired angle.

The angle of taper of cannula 10 on all sides may preferably be about 1.5 to 2 degrees, for example 1.6 to 1.7 degrees.

Thus, when the smaller, beveled distal portion 98 of cannula 10 enters through the skin of a patient, dilating through a preformed track, this creates less trauma to the patient, while the larger, proximal end 13 of cannula 10 provides a reduction in flow resistance that makes possible increased flow rates at pressures which are substantially lower than would be found with corresponding cannulas that are cylindrical and of the diameter of distal end 14 or slightly larger.

FIG. 1a shows a similar set with numbered references corresponding to those in FIG. 1 numbered with suffix "a". Instead of a bevel 98 and dull point 99, beveled distal portion 14 comprising FIG. 1a shows a non-beveled end 14a. Such end 14a comprises straight cut that is radiused or not, as desired. This shape is not capable, typically, to provide dilation of a preformed track through the skin.

Figure 2:
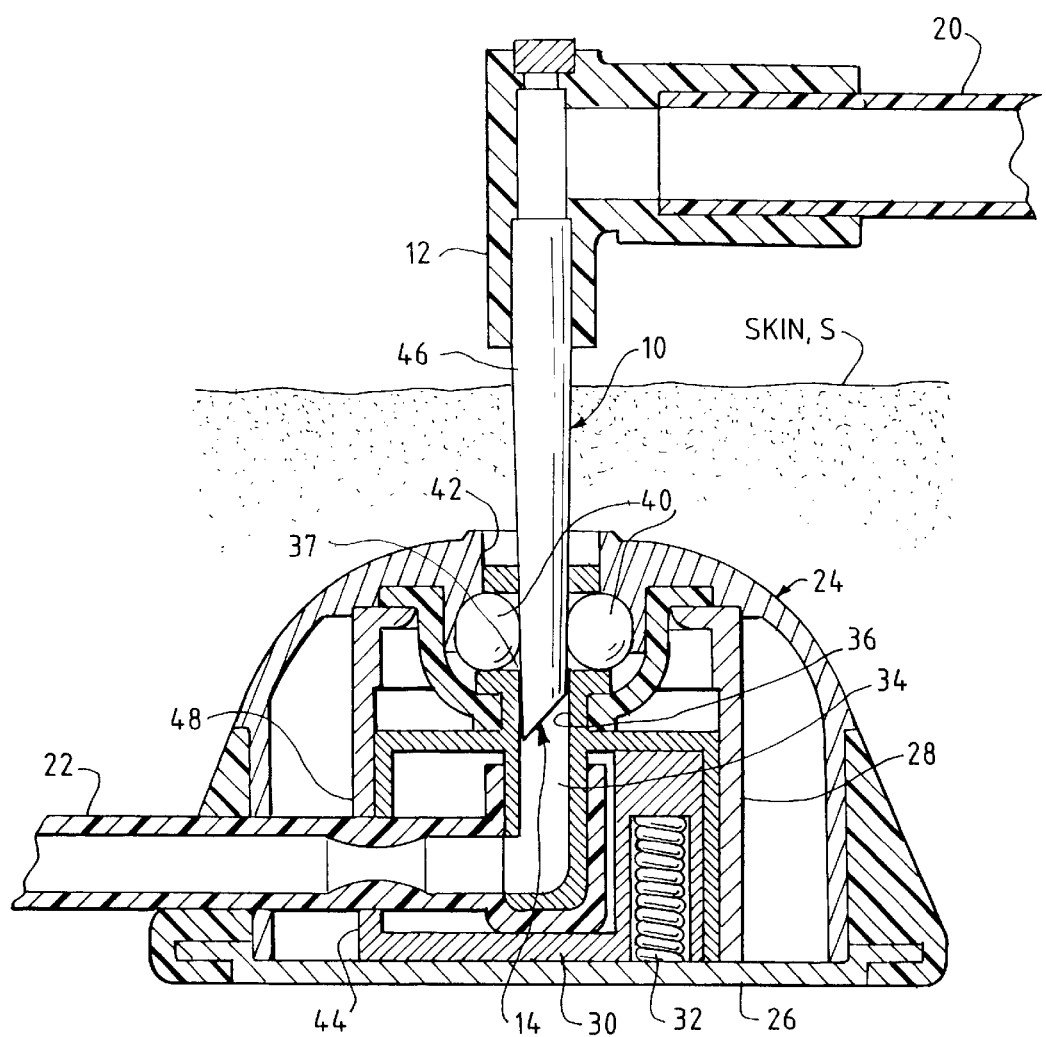
FIG. 2 is a substantially sectional view of an implanted artificial port for communication with the vascular system of a patient, shown to be in connection with the cannula of FIG. 1.

Referring to FIG. 2, tapered cannula 10 of this invention is shown to be engaging and communicating with an artificial port 24 which is implanted under the skin of a patient. Port 24 communicates through a conduit 22 to a blood vessel of the patient such as a large vein, or some other body lumen such as the liver, the lymphatic system, a body gland, or the like. Artificial port 24 may be of the design illustrated in PCT International Publication WO98/31416, published Jul. 23, 1998, the disclosures of which are incorporated by reference herein.

Artificial body access port 24 has a multi-part housing 26 as shown, which carries a frame 28 in which actuator block 30 slides upwardly and downwardly, being biased in the upward position by spring 32. As taught in the cited International Publication, actuator block 30 defines an axial bore 34 for receiving an ordinary needle. By this invention, bore 34 receives tapered cannula 10 of this invention. An upper portion 36 of axial bore 34 defines a taper, with the upper mouth portion 37 being wider than interior portions of bore 34.

Further as taught in the above cited International Application, a pair or more of balls 40 are caged within a circular aperture 42 within housing 30 and communicating with axial bore 34. Balls 40 are shown in their depressed position, being driven to that position by the advancement of the blunt, tapered needle 10 of this invention, which pushes the balls downwardly and then outwardly to the position shown, while also pushing actuator block 30 downwardly into the position shown and consequently depressing spring 32. By this act, tubing 22 is opened by the downward movement of pressure lip 44, away from upper lip 48, which is a part of frame 28 that retains the moving actuator block 30 in its two positions.

When needle 10 is not in position to spread balls 40, spring 32 causes actuator block 30 to rise to its upper position, with balls 40 moving inwardly and upwardly to an upper, constrained position, as taught and illustrated in the cited International Publication.

In accordance with this invention, cannula 10 is tapered as previously described, and in one embodiment has a beveled blunt end 14. Nevertheless, it is possible for any blunt, beveled or flat face cannula to depress and push aside balls 40, particularly when the contact angle between the balls and distal end 14 of cannula 10 is less than 50 degrees.

Preferably, the angle of taper of cannula 10 substantially matches the angle of taper of the tapered section 36 of axial bore 34. Thus, a luer-type seal is formed between bore 34 and tapered cannula 10, which, as is well-known, is fluid tight, yet relatively easy to disengage when that is desired. If it is further desired to provide added assurance as to the easy breakaway of the tapered seal between axial bore 34 and cannula 10, the inward taper of cannula 10 can be made to be slightly less, on the order of 0.1 degree, than the angle of taper of section 36 of axial bore 34. An adequate seal can still be created, but disengagement of the cannula from bore 34 can be done with less twisting force, when it is desirable to reduce twisting force on the implanted artificial port 24.

Blunt cannula 10 may pass along a tissue track (or "tract") 46 which is a permanent, usually closed passageway through the tissue of the patient, and which may be formed and maintained in accordance with the teachings of PCT International Publication WO99/03527, the disclosures of which are incorporated by reference herein. The closed tissue track 46 may typically be in the form of a curved slit in cross section.

Tapered beveled cannula 10 can easily pass through tissue track 46 and into sealing engagement with tapered surface 36, providing a reliable liquid seal with a low connection pressure on the order of one pound or less. In contrast, a product and system utilizing the implantable port 24 in conjunction with a cylindrical, non tapered needle otherwise similar to needle 10, 10a requires a pressure on the order of ten pounds in order to deform and force the distal tip of such a cylindrical needle into sealing engagement with tapered surface 36. Thus, by this invention, a solid but releasable seal between cannula 10 and artificial port 24 can be achieved without such high pressures. Also, because of the absence of such high pressures and distortion of the material adjacent to distal end 14 of cannula 10, cannula 10 can be reused if desired, for example being withdrawn and then immediately reused with the same patient, should the desirability or need arise for that.

Specifically, the permanent tissue track 46 may be formed by repeated penetrations by first a sharp cannula and then preferably a blunt cannula. It is believed that the tissue track (or tract) thus formed becomes lined with scar tissue or similar cells, and remains patent between successive events of access, in a manner similar to ear rings extending through pierced ears. Thus, a blunt cannula can be used for repeated access through the skin to an implanted port, of which port 24 is illustrative. By this technique, pain from needle stick can be greatly reduced, while the risk of infection of the tissue track can remain low.

Figure 3:
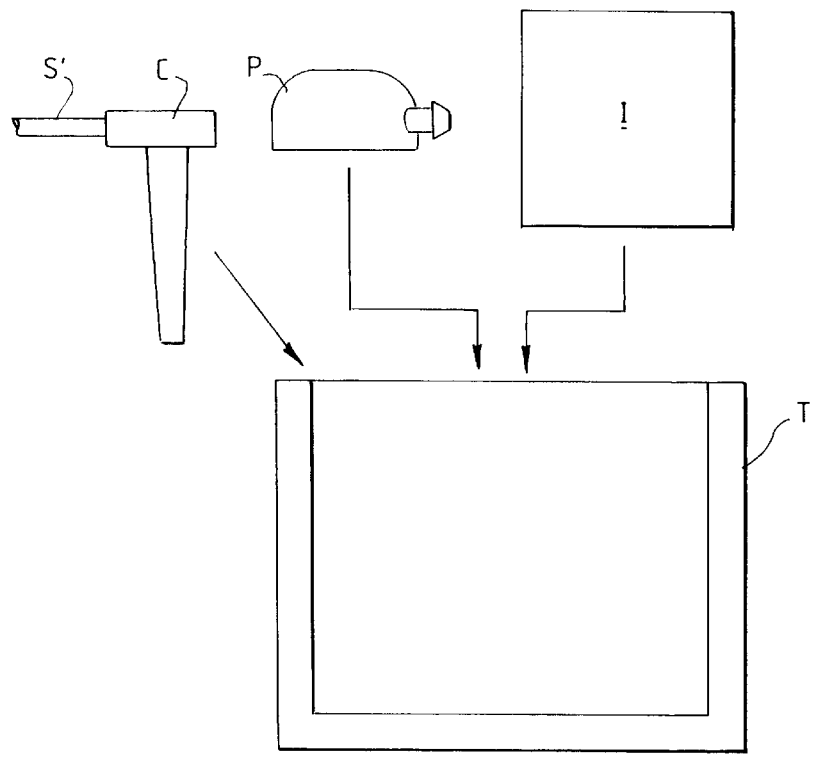
FIG. 3 shows a kit that incorporates the components of FIGS. 1 and 2, plus packaging and instructions.

Referring to FIG. 3, an implantable port P may be packaged together with instructions for use I in a kit. The kit components may include a cannula C in accordance with this invention, incorporated into a set for conveyance of blood if desired, or the cannula and port P may be packaged separately. Either one of the components, plus instructions for use I and added kit components, may be packaged in any suitable package T such as a tray, a box, and envelope, or the like, optionally capable of ethylene oxide sterilization or any other desired sterilization technique. Thus, a separate kit for cannula C and an attached set S' may be separately packaged in tray or other package T, or together with port P. Similarly, port P may be separately packaged from cannula C and any attached set S'. In either case, instructions for use are typically provided.

Figure 4:
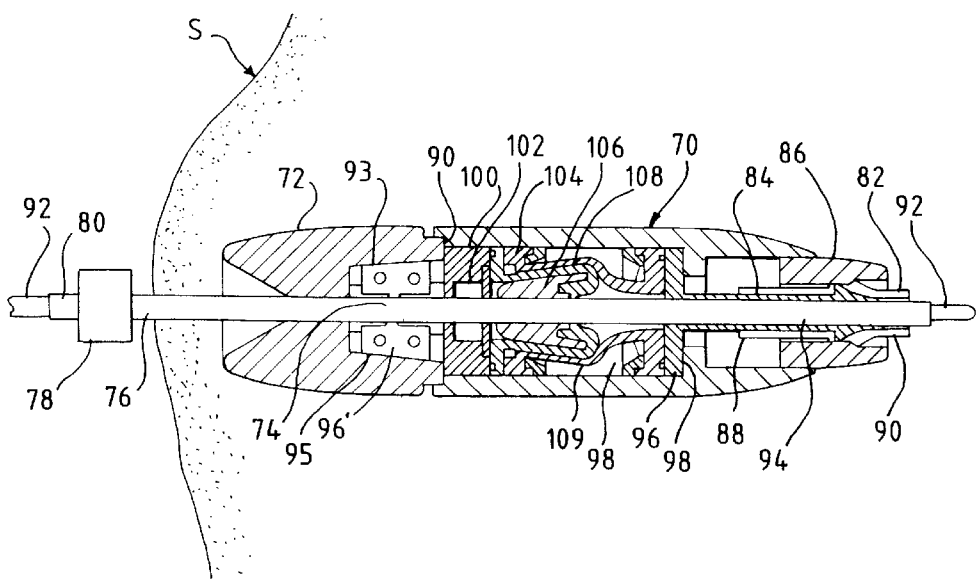
FIG. 4 is a longitudinal sectional view of another embodiment of implantable port which may be utilized in the invention, shown with a tapered cannula of this invention having a trocar.

Referring to FIG. 4, the tapered cannula of this invention may be used to provide access to an implantable port 70 of the design disclosed in PCT International Publication No. WO97/47338 of BioLink Corporation, the disclosures of which are incorporated by reference herein. Implantable port 70 comprises a housing 72 having a central lumen 74, to receive a cannula 76 which passes through the skin S of the patient and communicates with a hub 78 and a length of flexible tubing 80, to provide flow communication through port 70. Port 70 communicates with catheter tubing 82 at one end thereof, the catheter tubing being secured to port 70 by means of tube member 84, which frictionally retains catheter 82 against catheter locking element 86, while also defining a lumen of slightly frustroconical shape, tapering inwardly at an angle of about 1 to 4 degrees beginning at point 88 and tapering inwardly to point 90 at the distal end of tubular member 84.

If desired, cannula 76 may contain a sharp or a blunt trocar 92 (specifically shown to be in blunt form), which passes through the lumen of cannula 76 to facilitate cannula advancement, and is removed prior to use of the cannula.

Implanted artificial port 70 connects by catheter 82 to a body lumen such as a blood vessel in a manner similar to the previous embodiment. Multipart housing 72 comprises a lock assembly which in turn comprises silicone rubber plug 93, which defines a portion of lumen 74, and a plurality of typically three radially positioned locking blades 96 which are circumferentially flexible because of their mounting in silicone rubber member 94, but which can serve to lock cannula 76 until the cannula is twisted for removal, as taught in PCT International Publication No. WO97/47338, where port 70 is more fully described.

Housing 72 also defines a space 98 that receives and holds a needle guidance member 100, a cannula seal 102, a flexible valve seal 104, needle alignment member 106, flexible valve seal 108, and tubular seal 109. This arrangement provides both alignment and sealing for the advancing cannula 76.

As previously stated, tube member 84 is also provided, to provide further sealing and releasable locking of cannula 76.

Cannula 76 defines a distal section 94, which has a taper that matches the angle of taper of tubular segment 84 between points 88, 90, to form a tapered seal analogous to a luer connection, which both provides tight sealing and retention of cannula 76 within implanted port 70. This tapered conduit section 84 may have an integral flange 96 which is retained in position against shoulder 98 on one side and the other components such as tubular seal 109 on the other side. The angle of taper between points 88, 90 for both tube member 84 and cannula 76 can be about 1.6–1.7 degrees.

Figure 5:
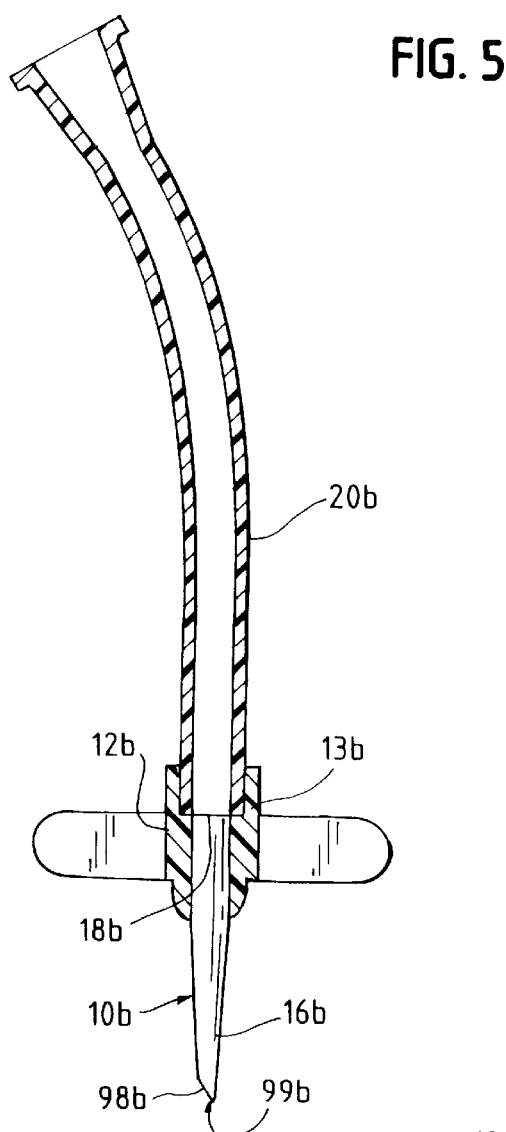
FIG. 5 is an elevational view of a fistula set for hemodialysis, manufactured in accordance with this invention.

Referring to FIG. 5, tapered cannula 10b is carried by a winged hub 12b, which also carries flexible tubing 20b of a fistula set, which is otherwise conventional except as otherwise described herein. Particularly, needle 10b is tapered in a manner similar to needle 10 so that its proximal end 13b has an inner diameter that is wider than its distal end 99b, with the lumen 16b of needle 10b continuously tapering inwardly from about 11 gauge at proximal end 13b to about 15 gauge at distal end 99b, by way of example.

Tapered hollow needle 10b defines a conventional bevel 98b or compound bevels or multibevels, which terminate in blunt point 99b, particularly a point which is incapable of cutting through intact, living tissue at 200 gm of pressure.

Figure 6:
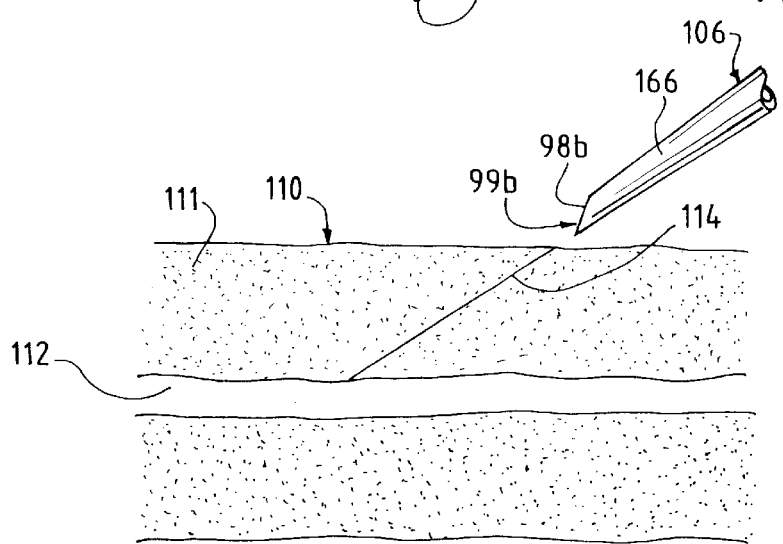
FIG. 6 is a sectional view showing how the blunt needle of the fistula set of FIG. 5 can penetrate a preformed track through the skin of a patient into blood flow connection with a vein or other body lumen.

Such a needle can be used in the manner illustrated in FIG. 6.

Cannula 10b of FIG. 5 is shown to be in position to penetrate the skin 110 of a patient and tissue and also to penetrate a vein 112 through a preformed "button hole" type of track or passageway 114 passing through tissue 111. As is known from publications authored by Zbylut J. Twardowski, a "button hole" preformed track can be made with a conventional trocar to penetrate a wall of vein 112, and the same track may be repeatedly used in a manner previously described until fibroid or scar tissue forms along track 114 to at least an extent. Then, blunt, hollow needles such as needle 10b may repeatedly and frequently pass through passageway of track 114 to enter into fluid exchange relationship with vein 112. Beveled tip 98b of needle 10b and its blunt, pointed end 99b, serve to permit the needle to open up track 114 and spread it as the needle passes into track 114, until the end 98b of lumen 16b comes into flow contact with vein 112. When needle 10b is withdrawn, track or passageway 114 generally shrinks back to an impassible track in slit form, which is filled with clotted blood, remaining in that condition until penetration by another beveled needle takes place.

By this invention, the taper of needle 10b, which may be from about 1–4 degrees per side, provides the advantages described above of a distal portion which is not too large to inflict severe discomfort on the patient, and a proximal portion having a large lumen for a significant relief of pressures at high flows.

Specifically, the term "blunt" for purposes of this invention can describe a cannula that cannot penetrate a single thickness of DuPont Linear Low Density Polyethylene SCLAIRFILM of 0.004 inch (essentially 0.1 mm) thickness at a pressure of 70 gm., or, if desired 100 gm where so stated. Such cannulas do not generally penetrate human skin in typical circumstances where accidental needle sticks may take place.

The above has been offered for illustrative purposes only, and is not intended to limit the scope of the invention of this application, which is as defined in the claims below.

That which is claimed:

1. A generally rigid cannula for communication through the skin with a body lumen of a patient including an entrance conduit, said cannula having a proximal end connected with a flow tube, said cannula having an inward taper of its outer wall extending at least most of the length between said proximal end and a distal end, whereby said distal end is of less diameter than said proximal end and said distal end being blunt wherein said tapered and blunt distal end is effectively incapable of cutting through living tissue and the tapered distal end adapted to be received by the entrance conduit that includes a generally corresponding shape to the tapered distal end forming a readily removable seal and locking connection with the entrance conduit.

2. The cannula of claim 1 in which said flow tube extends from said cannula at a substantially transverse angle to said cannula.

3. The cannula of claim 1 in which said inward taper extends substantially the entire cannula length.

4. The cannula of claim 1 in which said taper defines an angle of 1–4 degrees per side to the cannula longitudinal axis.

5. The cannula of claim 1 in which said distal cannula end is 11–13 gauge and said proximal cannula end is 14–15 gauge.

6. The cannula of claim 1 in which the cannula has a single lumen, and said lumen receives a removable trocar.

7. The cannula of claim 1 which the cannula has no bevel at a distal end thereof.

8. A kit comprising:
the cannula of claim 1;
instructions for use of the cannula with a patient; and
a package containing the cannula and the instructions for use.

9. The cannula of claim 1 in which said flow tube extends from said cannula at a substantially transverse angle to said cannula, and said inward taper extends substantially the entire cannula length.

10. The cannula of claim 9 in which said taper defines an angle of 1–3 degrees per side to the cannula longitudinal axis.

11. The cannula of claim 10 in which said distal cannula end is 11–13 gauge and said proximal cannula end is 14–15 gauge.

12. The cannula of claim 11 in which said cannula has a blunt distal cannula end and has a single lumen, and said lumen receives a removable trocar.

13. The cannula and trocar of claim 12, said trocar having a blunt forward end, incapable of effectively cutting through living tissue.

14. The cannula of claim 1 wherein an inner wall of the cannula has an inward taper.

15. A kit comprising at least one of a cannula and an implantable artificial port for communication with a body lumen of a patient, said artificial port having an entrance conduit which comprises a generally rigid, inwardly tapering section, said cannula having a proximal end connected with a fluid flow tube and a tapered distal end having a shape generally corresponding to said entrance conduit and being sized and proportioned to substantially match and seal with said inwardly tapering section of the entrance conduit, whereby said cannula can form a readily removable seal and locking connection with said inwardly tapering section;

said kit also comprising instructions for use setting forth a method of providing an external fluid connection with an implanted artificial port communicating with a body lumen of a patient, said artificial port having an entrance conduit which comprises a generally rigid, inwardly tapering section, which method comprises:

passing a tapered cannula through tissue of the patient into said entrance conduit, said tapered cannula having a proximal end connected with a fluid flow tube, between said proximal end and a distal end, said inward taper being sized and proportioned to substantially match and seal with said inwardly tapering section of the entrance conduit, whereby said cannula can form a readily removable seal with said inwardly tapering section; and a package containing said at least one of said tapered cannula and artificial port and the instructions for use.

16. The kit of claim 15 which comprises said cannula.

17. The kit of claim 15 which comprises said artificial port.

18. The cannula of claim 15 wherein an inner wall of the cannula has an inward taper.

* * * * *